(12) United States Patent
Schäfer et al.

(10) Patent No.: US 8,785,716 B2
(45) Date of Patent: Jul. 22, 2014

(54) ABSORBENT GARMENT WITH STRAIN RESISTANT CORE COVER

(75) Inventors: Jochen Schäfer, Schwalbach (DE); Mattias Schmidt, Idstein (DE); Nicole Graf, Bensheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 1104 days.

(21) Appl. No.: 12/431,807

(22) Filed: Apr. 29, 2009

(65) Prior Publication Data

US 2009/0270826 A1    Oct. 29, 2009

(30) Foreign Application Priority Data

Apr. 29, 2008  (EP) ..................................... 08103761

(51) Int. Cl.
  *A61F 13/15*    (2006.01)
  *A61F 13/537*   (2006.01)
  *A61F 13/531*   (2006.01)
  *A61F 13/532*   (2006.01)
  *A61F 13/534*   (2006.01)

(52) U.S. Cl.
  CPC ............ *A61F 13/15* (2013.01); *A61F 13/5376* (2013.01); *A61F 13/531* (2013.01); *A61F 2013/53463* (2013.01); *A61F 2013/15552* (2013.01); *A61F 13/5323* (2013.01); *A61F 13/534* (2013.01)
  USPC .......................................... 604/378; 604/365

(58) Field of Classification Search
  CPC . A61F 13/531; A61F 13/5323; A61F 13/534; A61F 13/5376; A61F 2013/15552; A61F 2013/53463
  USPC .................................. 604/365–366, 378, 383
  See application file for complete search history.

(56) References Cited

U.S. PATENT DOCUMENTS

| 5,221,274 A | 6/1993 | Buell et al. |
| 5,246,433 A | 9/1993 | Hasse et al. |
| 5,554,145 A | 9/1996 | Roe et al. |
| 2006/0247595 A1* | 11/2006 | Kawakami ..................... 604/390 |
| 2007/0038195 A1* | 2/2007 | Fuchs et al. .................. 604/366 |
| 2007/0093768 A1 | 4/2007 | Roe et al. |
| 2007/0167928 A1 | 7/2007 | Becker et al. |
| 2008/0312617 A1 | 12/2008 | Hundorf et al. |

FOREIGN PATENT DOCUMENTS

| EP | 0 953 324 A1 | 11/1999 |
| EP | 1 447 066 A1 | 8/2004 |
| EP | 1 774 940 A1 | 4/2007 |
| JP | 2003-129363 A | 5/2003 |
| JP | 2005-211135 A | 8/2005 |
| JP | 2007-075502 A | 3/2007 |

OTHER PUBLICATIONS

PCT International Search Report and Written Opinion, PCT/US2009/041949, date of mailing Apr. 28, 2009.

* cited by examiner

*Primary Examiner* — Lynne Anderson
(74) *Attorney, Agent, or Firm* — Christian M. Best; Charles R. Ware

(57) ABSTRACT

The present disclosure relates to an absorbent garment comprising an absorbent core having a nonwoven core cover that offers improved performance on holding back fine particulate material after having been exposed to external strain.

20 Claims, 2 Drawing Sheets

ABSORBENT GARMENT WITH STRAIN RESISTANT CORE COVER

FIELD

The present disclosure relates to an absorbent garment comprising an absorbent core having a nonwoven core cover that offers improved performance on holding back fine particulate material after having been exposed to external strain.

BACKGROUND

In absorbent garments nonwoven fabrics are commonly used as a core cover to enclose the absorbent core. When used as core cover, the nonwoven fabric should contain the absorbent material that commonly comprises superabsorbent polymer material (SAP), which is typically applied as a powder or as fine particulate material. The core cover should be designed to contain this material in a dry state prior to use and also in use when the absorbent material may be contacted with bodily fluids.

In recent years effort has been made to decrease the amount of cellulose fibers, such as fluff pulp, used for the so-called "airfelt" in absorbent cores. Decreasing the amount is desirable for reasons of comfort and appearance due to less bulk in the crotch region. Furthermore absorbent garments with reduced airfelt content occupy less storage space on the shelf, because they are thinner in the dry state prior to use.

The airfelt in conventional absorbent cores partly helps to immobilize the superabsorbent polymer material (SAP) in dry and wet states as the SAP particles are entangled between the airfelt fibers. Therefore, when the content of airfelt is reduced, other SAP-immobilization techniques are employed. For example in EP 1 447 066 (Busam et al.) SAP is adhered to a substrate layer by using thermoplastic adhesive.

However, absorbent cores that contain a high percentage of SAP still tend to be more likely to show a loss of SAP. Particularly in articles featuring an apertured topsheet, SAP lost from the core may get outside of the article and, when swollen due to the exposure to bodily fluids, stick to the wearer's skin (so-called "gel on skin"), which is undesirable.

SUMMARY

The present disclosure relates to an absorbent garment comprising an absorbent core having a nonwoven core cover that offers improved performance on holding back fine particulate material, such as superabsorbent polymer material, after having been exposed to external strain, e.g. process strains or in-use strains.

DETAILED DESCRIPTION

Definitions

Figure 1:
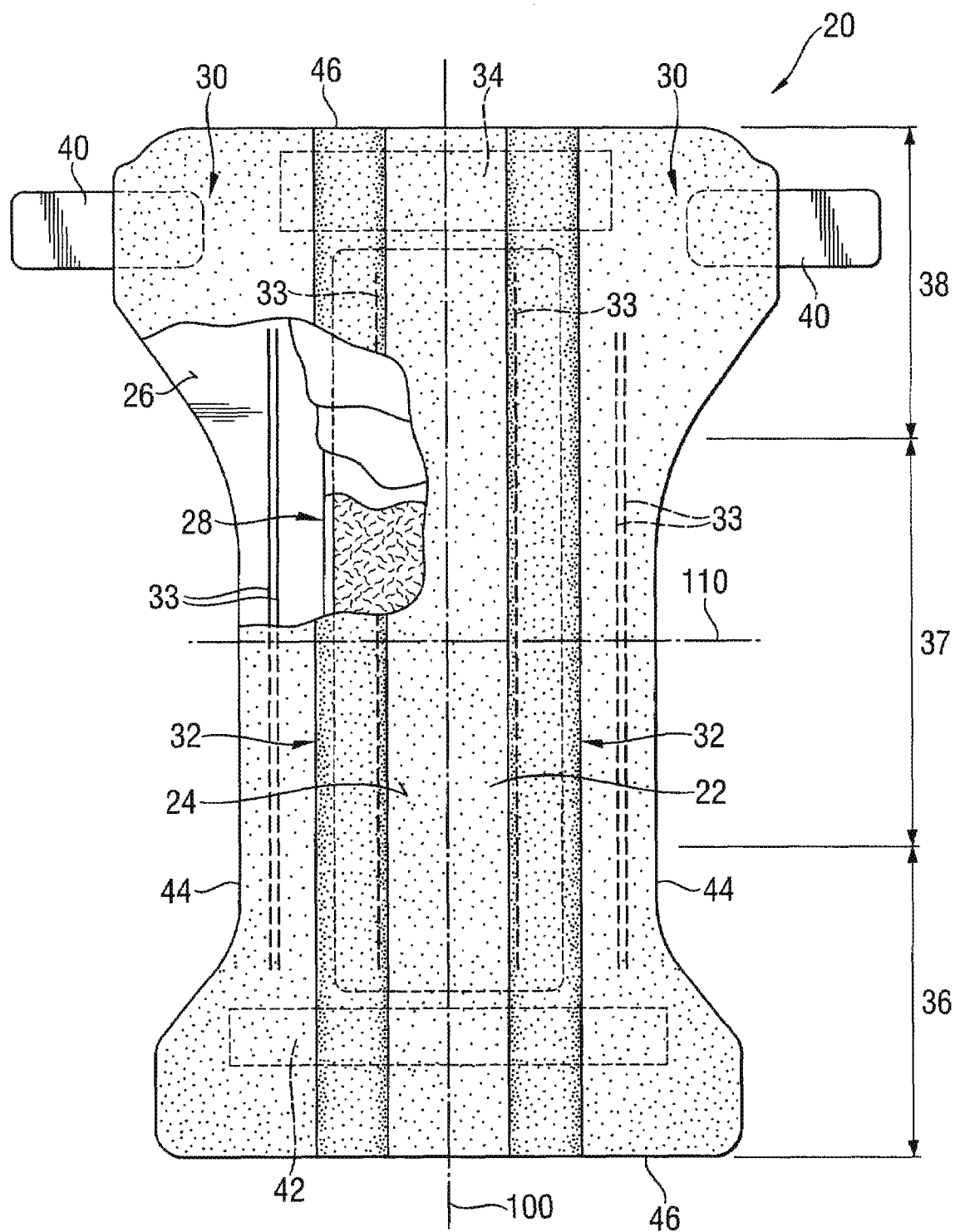
FIG. 1 shows an absorbent garment including an absorbent core with a core cover configured according to embodiments of the present disclosure.

As used herein, the following terms have the following meanings:

"Absorbent article" refers to articles that absorb and contain liquid. In one embodiment, the term "absorbent article" refers to articles that are placed against or in proximity to the body of the wearer to absorb and contain the various exudates discharged from the body. Absorbent articles include but are not limited to diapers, adult incontinent briefs, training pants, diaper holders and liners, sanitary napkins and the like.

"Absorbent garment" refers to an absorbent article that is intended to be worn by a wearer about the lower torso to absorb and contain the various exudates discharged from the body. Typically, an absorbent garment according to the present disclosure is disposable, however an absorbent garment can also be configured to be reusable.

"Diaper" refers to an absorbent garment generally worn by infants (e.g. babies or toddlers) about the lower torso. Suitable diapers are disclosed in, U.S. Pat. No. 5,221,274 issued to Buell et al. on Jun. 22, 1993; and U.S. Pat. No. 5,554,145 issued to Roe et al. on Sep. 10, 1996. As used herein the term "diaper" also comprises "pant-like diapers": A pant-like diaper refers to an absorbent garment having fixed sides and leg openings or to a side-fastenable absorbent garment. Suitable pant-like diapers are disclosed in, U.S. Pat. No. 5,246,433, issued to Hasse, et al. on Sep. 21, 1993.

"Disposable" refers to items that are intended to be discarded after a limited number of uses, frequently a single use (i.e., the original absorbent article as a whole is not intended to be laundered or reused as an absorbent article, although certain materials or portions of the absorbent article may be recycled, reused, or composted). For example, certain disposable absorbent articles may be temporarily restored to substantially full functionality through the use of removable/replaceable components but the article is nevertheless considered to be disposable because the entire article is intended to be discarded after a limited number of uses.

"Absorbent core" refers to the structure and/or material of an absorbent article that is intended to absorb and store exudates discharged from the body. Generally, the absorbent core comprises an absorbent material, such as a superabsorbent polymer.

"Core cover" refers to a fabric, such as a nonwoven fabric, which is intended to at least partly cover and/or enclose an absorbent material of an absorbent core.

"Nonwoven fabric" refers to a manufactured web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin. They may be staple or continuous filaments or be formed in situ. The terms "nonwoven fabric" and "nonwoven web" are used interchangeably in the present disclosure. The basis weight of nonwoven fabrics is usually expressed in grams per square meter (g/m$^2$) and can be determined according to European Disposables and Nonwovens Association (EDANA) method 40.3-90. Generally, nonwoven fabrics may comprise fibers made by nature (natural fibers), made by man (synthetic fibers), or combinations thereof. Example natural fibers include but are not limited to: animal fibers such as wool, silk, fur, and hair; vegetable fibers such as cellulose, cotton, flax, linen, and hemp; and certain naturally occurring mineral fibers.

As used herein "strain" refers to the first substantial elongation of a nonwoven fabric to a length exceeding its initial length, wherein the initial length is the length of a sample of the nonwoven fabric directly after its manufacture. However, nonwovens may experience some minor, generally unintended elongations (insubstantial elongations) after manufacture. For example, the nonwoven fabric is wound up on a roll by the supplier. Insubstantial elongations typically do not extend the nonwoven to more than its initial length plus 2% or even only 1% of its initial length.

Herein "hot melt adhesive" is used according to the definition given in "Adhesion and Adhesives Technology An Introduction" by Alphonsus V. Pocius (Hanser publishers Munich, 1997). Therein a hot melt is defined as an adhesive applied as a melt and gaining strength upon solidification.

Absorbent Garments

FIG. 1 is a plan view of a diaper 20 as an embodiment of an absorbent garment according to the present disclosure. The diaper 20 is shown in its flat out, uncontracted state (i.e., without elastic induced contraction). Portions of the structure are cut away to more clearly show the underlying structure of the diaper 20. The portion of the diaper 20 that contacts a wearer is facing the viewer.

The chassis 22 of the diaper 20 in FIG. 1 comprises the main body of the diaper 20. The chassis 22 comprises an outer covering including a liquid pervious topsheet 24 and/or a liquid impervious backsheet 26. The chassis 22 may also include most or all of the absorbent core 28 encased between the topsheet 24 and the backsheet 26. The chassis 22 may further include side panels 30, leg cuffs 32 with elastic members 33 and a waist feature 34. The leg cuffs 32 and the waist feature 34 typically comprise elastic members.

One end portion of the diaper is configured as the front waist region 36 of the diaper 20. The opposite end portion is configured as the rear waist region 38 of the diaper 20. The intermediate portion of the diaper is configured as the crotch region 37, which extends longitudinally between the front and rear waist regions. The crotch region 37 is that portion of the diaper 20 which, when the diaper is worn, is generally positioned between the wearer's legs. The waist regions 36 and 38 may include a fastening system comprising fastening members 40 preferably attached to the rear waist region 38 and a landing zone 42 attached to the front waist region 36.

The diaper 20 has a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

In one embodiment the topsheet of the absorbent garment of the present disclosure can also be apertured, i.e. the topsheet can have a plurality of apertures having an aperture size of at least about 0.2 mm$^2$. The topsheet may have an open area of at least about 10%, the open area being the sum of all apertures. The Method to determine the aperture size and open area of the apertured topsheet in context of the present disclosure is disclosed in EP 0953324.

In certain embodiments at least a part of the topsheet is apertured; for example apertured in at least 20%, or 50%, or 80%, or 90%, or 100% of the area overlaying the absorbent core. Due to the apertures, the topsheet may not function as a second barrier for the SAP particles. Accordingly, embodiments of the present disclosure describe an absorbent core with improved SAP retaining properties for absorbent garments comprising an apertured topsheet.

A diaper may also include other features as are known in the art including front and rear ear panels, waist cap features, elastics and the like, to provide better fit, containment and aesthetic characteristics.

Absorbent Core

An absorbent core has two sides: an upper, body-facing side and a lower, garment-facing side. Furthermore an absorbent core comprises a core cover and absorbent material, comprising at least the SAP. According to the present disclosure, the core cover, as described herein, may be used at least on one side of the absorbent core to cover at least a portion, or substantially all, or all of the respective side of the absorbent material.

Additionally, the core cover may also be used to cover at least a portion, or substantially all, or all of the body-facing side and the garment-facing side of the absorbent material, such that the absorbent material is wrapped by the core cover. In these embodiments the absorbent material may either be sandwiched between two separately provided sheets of core cover material, or wrapped by folding one sheet of core cover material, for example in a C-fold, to envelope the absorbent material.

When the nonwoven is intended to cover the body facing side of the absorbent core it may be desirable for the nonwoven to be hydrophilic. In certain embodiments of the present disclosure the nonwoven may be rendered hydrophilic by means known in the art.

In an alternative embodiment, the core cover may be used to cover only the garment-facing side of the absorbent material. However, in certain embodiments it may be preferred that the core cover described below covers the body-facing side of the absorbent material. In embodiments wherein a core cover comprises two separately provided sheets of material, at least one of the sheets can include a core cover material of the present disclosure.

In embodiments wherein a core cover comprises a single sheet of core cover material, the edges of the folded sheet may be sealed together to enclose the absorbent material. Sealing may be facilitated at least along the longitudinal edges of the absorbent core. Alternatively, the core cover may be sealed completely along all edges.

The amounts of materials used in the absorbent core herein are given in percent (%) by weight relative to the basis weight of the whole absorbent core. The whole absorbent core herein includes the core cover.

An absorbent core may comprise any absorbent material that is generally compressible, conformable, non-irritating to the wearer's skin, and capable of absorbing and retaining liquids such as urine and other certain body exudates. An absorbent core may comprise a wide variety of liquid-absorbent materials commonly used in disposable diapers or other absorbent articles. For example soft materials providing a rather fluffy structure with a lot of empty space, such as comminuted wood pulp, creped cellulose wadding, chemically stiffened, modified or cross-linked cellulosic fibers which are generally referred to as "airfelt". However, the absorbent core of the present disclosure preferably comprises less than 20%, or 15% or 10% or 5% by weight the absorbent core of such an airfelt material. The absorbent core may also be substantially free of, or completely free of airfelt material wherein "substantially free of" means that less than 1% by weight of the absorbent core is airfelt material and "completely free of" means that 0% by weight of the absorbent core is airfelt material.

The absorbent material typically comprises SAP, e.g. in the form of SAP particles, optionally mixed with fibrous materials. The absorbent core may comprise a relatively high amount of SAP of more than 80% or 85% or 90% or 95% by weight of the absorbent core. Furthermore, the absorbent core may comprise a hot melt adhesive, as will be described in more detail below. According to one embodiment of the present disclosure, the absorbent core comprises the superabsorbent polymer material, the hot melt adhesive and the core cover, wherein the amounts of these materials add up to present 99% or 100% by weight of the absorbent core.

An absorbent core according to the present disclosure may, for example, comprise a core cover, a first nonwoven fabric, and a second nonwoven fabric, wherein the SAP may be deposited on the first and second nonwoven fabrics respectively and hot melt adhesive may be deposited in such a way that it at least partly covers or enlaces the deposited SAP on the respective first and second nonwoven fabrics. The absorbent core may then be incorporated in the absorbent garment in such that the first nonwoven fabric faces the topsheet. The first and optionally also the second nonwoven fabric may comprise the core cover of the present disclosure as will be described below.

It has now been found that production processes for absorbent cores comprising relatively high amounts of SAP of more than 80% or 85% or 90% or 95% by weight of the absorbent core and relatively low amounts of airfelt material of less than 20%, or 15% or 10% or 5% by weight of the absorbent core, and especially absorbent cores that are substantially free or even completely free of airfelt material, often involve steps where the core cover is exposed to higher strain compared to processes used for the production of conventional cores having comparably high amount of airfelt. These strains may cause damages, especially holes in the nonwoven fabric due to the rupture of fibers, and lead to an increased escape of SAP particles through these holes. An exemplary production process is described below.

Further, an increased loss of SAP may occur when the article is in use. Due to uptake of fluids the SAP swells, tends to expand and may then be hydraulically forced through the core cover. This effect is even more pronounced in cores where the SAP particles are adhered to the core cover by hot melt adhesive, especially if the SAP particles are encapsulated or enlaced by the hot melt adhesive. Due to this encapsulation, the SAP particles may expand by tearing a hole through the core cover, since the expansion in other directions (away from the core cover) is hindered by the hot melt adhesive. This loss may cause the superabsorbent material to stick to a wearer's skin, a phenomenon commonly referred to as "gel on skin".

In view of the above-mentioned reasons core covers should be able to provide sufficient strength and integrity to survive strain intense production processes without substantial damage resulting in holes in the nonwoven and in loss of SAP through these holes. Therefore, a core cover of the present disclosure should retain the relatively small SAP particles of the superabsorbent polymer material and simultaneously provide a strain resistant fabric that can be effectively employed in fast, strain intense production processes. Furthermore the core cover used in the process of the present disclosure should withstand the exposure to strain when the absorbent article is in use, for example due to swelling of the superabsorbent polymer material.

Core Cover

The core cover of the present disclosure is a nonwoven fabric made of synthetic fibers.

Synthetic fibers are man-made fibers, comprising fibers derived from natural sources and mineral sources. Example synthetic fibers, which are derived from natural sources include but are not limited to viscose, polysaccharides (such as starch), rayon and lyocell. Example fibers from mineral sources include but are not limited to polyolefin (such as polypropylene or polyethylene) fibers and polyester fibers. Fibers from mineral sources are derived from petroleum.

Nonwoven webs can be formed by direct extrusion processes during which the fibers and webs are formed at about the same point in time, or by preformed fibers which can be laid into webs at a distinctly subsequent point in time. Example direct extrusion processes include but are not limited to: spunbonding, meltblowing, solvent spinning, electrospinning, and combinations thereof. Nonwoven webs often comprise several layers, which may be made from different extrusion processes.

As used herein, the term "spunbonded fibers" refers to small diameter fibers, which are formed by extruding molten thermoplastic material as filaments from a plurality of fine, usually circular capillaries of a spinneret. Spunbond fibers are quenched and generally are not tacky when they are deposited onto a collecting surface. Spunbond fibers are generally continuous. The spunbond fibers herein may have diameters from 10 μm to 40 μm.

As used herein, the term "meltblown fibers" means fibers formed by extruding a molten thermoplastic material through a plurality of fine, usually circular, die capillaries as molten threads or filaments into converging high velocity gas (e.g. air) streams, which attenuate the filaments of molten thermoplastic material to reduce their diameter. Thereafter, the meltblown fibers are carried by the high velocity gas stream and are deposited on a collecting surface to form a web of randomly dispersed meltblown fibers. The meltblown fibers herein may have diameters from 0.2 μm to 10 μm.

Example "laying" processes include wet-laying and dry-laying. Example dry-laying processes include but are not limited to air-laying, carding, and combinations thereof typically forming layers. Combinations of the above processes yield nonwovens commonly called hybrids or composites.

The term "nonwoven layer" refers to a layer of fibers that has been extruded by the same technique and have been laid down in a single step. Herein "nonwoven layer of meltblown/spunbond fibers" and "meltblown/spunbond layer" are used interchangeably.

The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bonds, thermal bonds, pressure bonds or by combinations thereof.

While spunbond webs provide relatively good resistance to strain, they offer rather poor area coverage, especially in nonwovens having relatively low basis weights, resulting in pores large enough for the SAP to escape. Furthermore, a spunbond nonwoven having a relatively high basis weight, which may provide better area coverage, may not work well as a core cover because of its relatively high stiffness and relatively low water permeability. Additionally it may be more difficult to render a spunbond web with high basis weight hydrophilic. In embodiments where the body facing side of the absorbent core is covered by the core cover it is desirable that the core cover is water permeable and hydrophilic. Meltblown layers, due to their smaller average pore size, may be suitable to contain even very small particles, but break or rupture more easily when exposed to strain and offer poor abrasion resistance.

The nonwoven web used for the core cover may comprise three or more nonwoven layers each either consisting of spunbond or meltblown fibers. At least two layers consist of spunbond fibers and one or more of meltblown fibers. The nonwoven layers are arranged in that the one or more meltblown layers are sandwiched between the two or more spunbond layers.

In one embodiment the core cover may comprise three layers, wherein two layers may comprise spunbond fibers (S), one layer may comprise meltblown fibers (M) and wherein the meltblown layer is sandwiched between the spunbond layers, forming a configuration known as SMS. Alternatively, the core cover may comprise four layers, wherein two layers may comprise spunbond fibers, two layers may comprises meltblown fibers and wherein the meltblown layers are sandwiched between the spunbond layers, forming a configuration known as SMMS. In another embodiment the core cover may comprise five or more nonwoven layers, wherein two or more nonwoven layers may comprise spunbond fibers and two, or three, or more nonwoven layers may comprise meltblown fibers and wherein the meltblown layers are sandwiched between the spunbond layers, such as SSMMS, SMMMS, SSMMMS or the like.

It has now been found that by adjusting the ratio of spunbond to meltblown fibers in a nonwoven core cover the retention of SAP can be improved even after the nonwoven has been exposed to strain. Therefore, this ratio may be effectively used to adjust the nonwoven to the requirements of strain intense production processes. In such a nonwoven the spunbond fibers act as an efficient scaffold which is able to stabilize the one or more layers of meltblown fibers. The meltblown fibers on the other side provide a fine net which retains the SAP.

The total basis weight of the nonwoven fabric used for the core cover should be high enough to ensure good area coverage and to provide sufficiently small pores. On the other hand the basis weight should not be too high, so that the nonwoven is still compliant and non-irritating to the skin of the wearer. In preferred embodiments, the total basis weight may range from 8 to 20 g/m$^2$, or 9 to 16 g/m$^2$, or 10 to 14 g/m$^2$, for example 13 g/m$^2$.

The amount of the spunbond nonwoven fibers in a nonwoven fabric consisting of spunbond and meltblown fibers may be selected such that the content of spunbond fibers ranges from 80 to 95%, or 82 to 90% of the total basis weight of the nonwoven fabric. It has been found that a rather high content of spunbond fibers increases the strain resistance of the nonwoven fabric and helps to reduce the areas in the meltblown layers that are damaged or ruptured when the web is exposed to strain. It has also been found, that in such a core cover even a relatively low amount of meltblown fibers is sufficient for retaining relatively small particles, even after the nonwoven has been strained.

The nonwoven fabric used for the core cover is further characterized in that it does not show large holes after having been exposed to strain, enabling it to effectively retain the SAP during production of the absorbent article and during use. As characterized by air permeability before and after defined straining determined by the method given in the Test Methods section, the nonwoven web of the present disclosure should show an increase in air permeability of less than 18% after having been strained by $\epsilon=10\%$ (wherein $\epsilon$ is prescribed strain, as explained in Test Methods), or less than 20% after having been strained by $\epsilon=15\%$.

The nonwoven fabric used for core cover of the present disclosure should effectively contain relatively small superabsorbent polymer particles and therefore, it should show an initial air permeability of at most 60 m$^3$/(m$^2$·min), or at most 50 m$^3$/(m$^2$·min), or at most 40 m$^3$/(m$^2$·min).

In certain embodiments the core may be formed by production processes where a vacuum is applied to the nonwoven fabric used for the core cover to hold it on a support and to temporarily immobilize deposited material on the nonwoven. In these embodiments it may be desirable that the nonwoven fabric has an initial air permeability of at least 5 m$^3$/(m$^2$·min), or at least 10 m$^3$/(m$^2$ min), or at least 20 m$^3$/(m$^2$ min).

Hot Melt Adhesive

The hot melt adhesive is typically present in a basis weight of 1-40 g/m$^2$ or 2-35 g/m$^2$, or 3-30 g/m$^2$.

Molecular weights herein are given in g/mol unless specified differently.

The hot melt adhesive 68 and 76 may serve to cover and at least partially immobilize the SAP 66 and 74. The hot melt adhesive may at least partially immobilize the SAP by covering or enlacing the SAP. In one embodiment of the present disclosure, the hot melt adhesive 68 and 76 can be disposed essentially uniformly with the SAP 66 and 74. However, in a certain embodiment, the hot melt adhesive 68 and 76 may be provided as a fibrous layer which is at least partially in contact with the SAP 66 and 74 and partially in contact with the nonwoven core cover 64 and 72.

Figure 2:
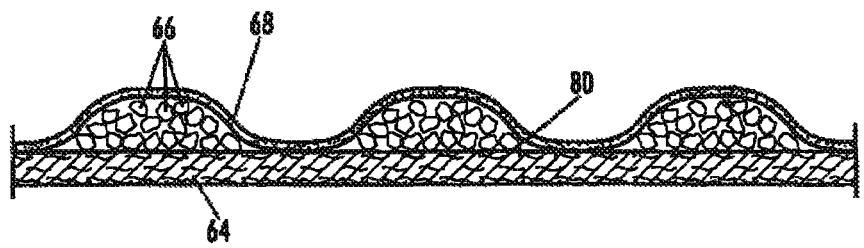
FIG. 2 shows an absorbent core with a core cover configured according to embodiments of the present disclosure.
Figure 3:
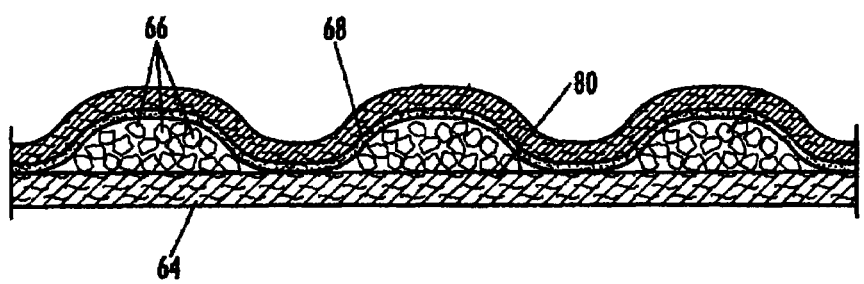
FIG. 3 shows another absorbent core with a core cover configured according to embodiments of the present disclosure.
Figure 4:
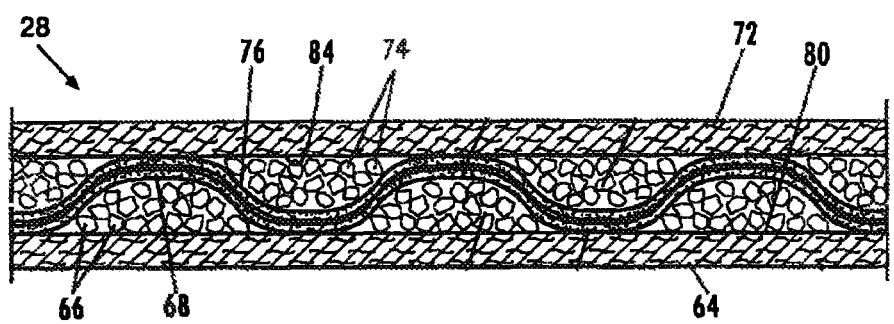
FIG. 4 shows a further absorbent core with a core cover configured according to embodiments of the present disclosure.

FIGS. 2, 3 and 4 show such a structure, and in that structure, the SAP 66 and 74 is provided as a discontinuous layer on a nonwoven core cover 64 and 72, and a layer of fibrous hot melt adhesive 68 and 76 is laid down onto the layer of SAP 66 and 74, such that the hot melt adhesive 68 and 76 is in direct contact with the SAP 66 and 74, but also in direct contact with a surface 80 and 84 of the nonwoven core cover 64 and 72, in areas where the nonwoven fabric is not covered by the SAP 66 and 74. This imparts an essentially three-dimensional structure to the fibrous layer of hot melt adhesive 68 and 76. In other words, the hot melt adhesive 68 and 76 undulates between the SAP 68 and 76 and the surface of the nonwoven core cover 64 and 72.

Thereby, the hot melt adhesive 68 and 76 may cover the SAP 66 and 74, and thereby immobilize this material. In a further aspect, the hot melt adhesive 68 and 76 bonds to the nonwoven core cover 64 and 72 and thus affixes the SAP 66 and 74 to the nonwoven core cover 64 and 72. Thus, in accordance with certain embodiments, the hot melt adhesive 68 and 76 immobilizes the SAP 66 and 74 when wet, such that the absorbent core 28 achieves a wet immobilization of more than about 50%, or more than about 60%, 70%, 80% or 90% according to the Wet Immobilization Test described in U.S. Appl. Ser. No. 60/936,102. Some hot melt adhesives will also penetrate into the nonwoven core cover 64 and 72, thus providing for further immobilization and affixation.

Of course, while the hot melt adhesives disclosed herein provide a much improved wet immobilization (i.e., immobilization of SAP when the article is wet or at least partially loaded), these hot melt adhesives may also provide a very good immobilization of SAP when the absorbent core 28 is dry.

The hot melt adhesive comprises at least one thermoplastic polymer in combination with other thermoplastic diluents such as tackifying resins, plasticizers and additives such as antioxidants.

In certain embodiments, the thermoplastic polymer typically has a weight average molecular weight (Mw) of more than 10,000 and a glass transition temperature ($T_g$) usually below room temperature (25° C.), or of less than 22° C., or less than 18° C., or less than 15° C. In certain embodiments $T_g$ may be above 0° C.>$T_g$. In embodiments where the thermoplastic polymer has more than one $T_g$ the values given refer to the lowest glass transition temperature. The thermoplastic polymer may also have a softening point, as determined by the ASTM Method D-36-95 "Ring and Ball", in the range between 50° C. and 300° C. In some embodiments the Mw of the thermoplastic polymer is less than 10,000,000.

In certain embodiments, typical concentrations of the thermoplastic polymer in a hot melt adhesive are in the range of about 20% to about 40% by weight of the hot melt adhesive.

Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

In exemplary embodiments, the tackifying resin has typically a Mw below 5,000 and a $T_g$ usually above room temperature (25° C.), typical concentrations of the tackifying resin in a hot melt are in the range of about 30% to about 60% by weight of the hot melt adhesive. In certain embodiments the tackifying resin has an Mw of more than 1,000.

The plasticizer has a low Mw of typically less than 1,000 and a $T_g$ below room temperature, with a typical concentration of about 0% to about 15% by weight of the hot melt adhesive. In certain embodiments the plasticizer has an Mw of more than 100.

In certain embodiments, the hot melt adhesive 68 and 76 is present in the form of fibers. In some embodiments, the fibers will have an average thickness of about 1 to about 50 micrometers or about 1 to about 35 micrometers and an average length of about 5 mm to about 50 mm or about 5 mm to about 30 mm.

Optionally, a part of the hot melt adhesive, for example an amount of 0-10 g/m$^2$, may already be deposited on the nonwoven core covers 64 and 72 before application of the SAP 66 and 74 for enhancing adhesion of both the SAP 66 and 74 and the rest of the hot melt adhesive 68 and 76, which is deposited after the SAP has been deposited, to the respective nonwoven core covers 64 and 72.

Said part of the hot melt adhesive may be applied to the nonwoven core covers 64 and 72 by any suitable means, but according to certain embodiments, may be applied in about 0.5 to about 1 mm wide slots spaced about 0.5 to about 2 mm apart.

Process for Making an Absorbent Core

An exemplary process for making an absorbent core that comprises at least a first nonwoven web and a superabsorbent polymer material (SAP) will now be described. The process comprises steps of (a) providing the first nonwoven web, (b) providing the SAP, (c) depositing the first nonwoven web on a support and (d) depositing the SAP on the first nonwoven web.

During the process, the first nonwoven web is strained by $\epsilon \geq 10\%$ of its initial length. This strain is the first substantial elongation the web undergoes after its manufacture. The strain may occur at any time during the production process and may be caused for example by the forces that are applied to hold the core cover on a support with an uneven or apertured surface. Such forces may for example be applied by vacuum means, pulling means (mechanically) or the like. The strain may as well be caused by laying down the SAP at high speed on the first nonwoven.

For the process as described in more detail in the section "core cover" is used as the first nonwoven web to ensure that the SAP will be retained effectively during the production process and in the final product.

The process may further comprise one or more steps of depositing hot melt adhesive. The hot melt adhesive may be deposited in the form of fibers such that it enlaces and at least partly immobilizes the SAP.

Additionally, the process may comprise steps of providing and depositing a second nonwoven web to cover the SAP and the hot melt adhesive. The second nonwoven may be deposited in such that the SAP and the hot melt adhesive are sandwiched between the first and the second nonwoven web.

Alternatively, the process may comprise a step wherein the first nonwoven is folded to wrap the SAP and the optional hot melt adhesive. The first nonwoven may be folded in such that the SAP and the hot melt adhesive are enveloped by the first nonwoven.

The steps of the process of the present disclosure will now be described in more detail.

(a) Providing the First Nonwoven Web

The nonwoven may be taken from a roll where it is wound up, or it may be used directly after its manufacture without intermediate storage.

(b) Providing the SAP

The SAP may be taken up from a reservoir, for example by a transfer device such as a hopper. The transfer device may have recesses on the surface that can for example determine the amount and distribution pattern of SAP taken up by the transfer device.

(c) Depositing the First Nonwoven Web on a Support

The first nonwoven web is deposited on the first side of the support. The support may possess an uneven or apertured surface. To provide an uneven surface, the support may comprise a plurality of indents or grooves. A suitable support for example may be a support grid. The support has a first and an opposing second side. Material, such as the first nonwoven, will be deposited on the first side. The deposited material may be held on the support by a drawing force, for example by gravitation, an air-stream or by a vacuum which can be applied on the second side of the support. Any apertured support on which deposited material can be held by means of passing air through the support herein may also be referred to as vented support.

The support may have the form of a plate, a grid or a belt, for example a rotating drum, a roll or a transport belt. In embodiments where the support is a drum, the first side of the support corresponds to the outside surface of the drum and the second side corresponds to the inside surface of the drum.

Due to the uneven or apertured surface of the support and the drawing force, the nonwoven may adopt an uneven shape; it may for example bulge corresponding to the apertures, indents or grooves.

(d) Depositing the Sap on the First Nonwoven Web

The SAP may be moved by the transfer device from the reservoir to the first nonwoven web where the SAP may be deposited on the first nonwoven web. The SAP may be deposited on the nonwoven in such an amount that the content of SAP in the finished absorbent core exceeds 80% or 85% or 90% or 95% by weight of the absorbent core.

Test Methods

Using a TexTest Instruments Air Permeability Tester FX 3300 LABOTESTER III (available from TexTest Instruments, Schwerzenbach, Switzerland) or equivalent, measure the air permeability of the samples according to EDANA 140.2-99 with the following settings.

Samples are conditioned 24 hours and measured at 23° C., 50% relative humidity. Samples that are intended to be strained are conditioned before the strain is applied. The straining has to be carried out at 23° C., 50% relative humidity as well.

Using a circular test area of 20 cm² and a pressure drop of Δp=125 Pa

Report results in m³/(m²·min) as the arithmetic mean of 5 single measurements taken on different samples.

Straining Method and Apparatus

The straining is suitably exercised with an apparatus as described in the following. A suitable device shall have two clamps. The two clamps have a longer edge defining their width. The width of the clamps is 200 mm and the clamps are capable of holding the test piece securely across their full width without damage. The clamps shall be oriented in such that their longer edges are parallel and shall be movable in a direction perpendicular to their longer edges. The device shall be capable of extending a test sample at a constant rate of 3 cm/sec to a predetermined length (by moving the two clamps away from each other, see below).

The clamps will be suitable to the task of securely holding the sample without damaging it and have a clampdown force enough to hold the sample securely without slippage in the strained mode, and have a smooth surface from which the areas of the sample in contact with the clamps will not be damaged.

The straining procedure shall consist of the following steps:

Cut a web sample to 50 cm length in the intended direction of straining, and 15 cm in the direction perpendicular to the direction of straining;

Secure the sample between the pair of clamps in such that the sample will be strained in machine direction of the nonwoven sample (machine direction being the direction of production of the nonwoven).

Move the second clamp away from the first clamp carefully just until the sample reaches its original full flat-out length, i.e. it should be wrinkle-free and without bows between the clamps, however the sample will not be strained during this step over its original length. Stop the clamps in the position when this state is reached. Measure and record the unstrained length $l_0$ as the edge-to-edge distance between the clamps (all lengths are suitably measured with an accuracy of +/−1 mm). The unstrained length $l_0$ should be 30 cm.

Strain the sample at a rate of about 3 cm/sec until the strained length $l=l_0+\Delta l$ is reached, measured as the edge-to-edge distance between the clamps, where $\Delta l=l_0\times\epsilon/100$ is the elongation and $\epsilon$ the prescribed strain (expressed in %). Stop the clamps in this position and hold them for between 1 and 3 seconds. Then move the clamps back to a position where the sample is hanging freely between them and not experiencing any strain, and remove the sample.

The air permeability of the strained samples shall be measured immediately after having strained them following the above procedure. The area of the sample submitted to air permeability testing shall be that which has been in the central position of the straining, i.e. at approximately equal distance between the two clamps in the direction of the straining, and between the free edges in the direction perpendicular to the direction of straining.

Unstrained samples shall be measured as obtained, e.g. from a roll. The samples are to be handled with care and no excessive crumpling or other mechanically stressful treatments should be exercised on them prior to measurement.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent garment comprising:
   an absorbent core, including a superabsorbent polymer material, a hot melt adhesive, and a core cover;
   wherein the core cover surrounds at least a part of the absorbent core and includes a nonwoven web;
   wherein the nonwoven web has:
      a layer of meltblown fibers sandwiched between two nonwoven layers of spunbonded fibers, and a weight of the spunbond fibers ranges from 80% to 95% of a basis weight of the nonwoven web;
      the basis weight ranging from 8 to 20 g/m² before being subjected to a first prescribed strain;
      an initial air permeability of less than 60 m³/(m²·min) before being subjected to a first prescribed strain; and
      a subsequent air permeability that is less than 18% greater than the initial air permeability after the nonwoven web is subjected to the first prescribed strain; and
   wherein the first prescribed strain is at least 10%.

2. The absorbent garment according to claim 1, wherein the basis weight of the nonwoven web ranges from 9 to 16 g/m².

3. The absorbent garment according to claim 1, wherein the weight of the spunbond fibers in the nonwoven web ranges from 82 to 90% of the basis weight of the nonwoven web.

4. The absorbent garment according to claim 1, wherein the absorbent core has a body-facing side and a garment-facing side and the core cover is only covering the body-facing side of the absorbent core.

5. The absorbent garment according to claim 1, wherein at least 80% of a weight of the absorbent core is from the superabsorbent polymer material, and the absorbent core includes about 1-40 g/m² of the hot melt adhesive.

6. The absorbent garment according to claim 1, further comprising a topsheet, wherein at least a portion of the topsheet is overlaying the absorbent core, and the overlaying portion is apertured.

7. The absorbent garment according to claim 1, wherein the absorbent garment is made by a process comprising a step wherein the core cover is strained.

8. The absorbent garment according to claim 1, wherein the absorbent core comprises less than 5% by weight of airfelt material.

9. The absorbent garment according to claim 1, wherein the absorbent core comprises more than 85% by weight of the superabsorbent polymer material.

10. The absorbent garment according to claim 1, wherein the absorbent core comprises more than 90% by weight of the superabsorbent polymer material.

11. The absorbent garment according to claim 1, wherein the absorbent core comprises more than 95% by weight of the superabsorbent polymer material.

12. The absorbent garment according to claim 11, wherein the absorbent core comprises less than 5% by weight of airfelt material.

13. The absorbent garment according to claim 1, wherein the superabsorbent polymer material, the hot melt adhesive, and the core cover together add up to at least 99% by weight of the absorbent core.

14. The absorbent garment according to claim 1, wherein the superabsorbent polymer material, the hot melt adhesive, and the core cover together add up to 100% by weight of the absorbent core.

15. An absorbent garment comprising:
an absorbent core comprising a superabsorbent polymer material, a hot melt adhesive, and a core cover, wherein the superabsorbent polymer material is more than 80% by weight of the absorbent core, wherein the core cover surrounds at least a portion of the absorbent core and includes a nonwoven web, and wherein the nonwoven web has:
a layer of meltblown fibers sandwiched between two nonwoven layers of spunbonded fibers, and a weight of the spunbond fibers ranges from 80% to 95% of a basis weight of the nonwoven web;
the basis weight ranging from 8 to 20 $g/m^2$ before being subjected to a prescribed strain;
an initial air permeability of less than 60 $m^3/(m^2 \cdot min)$ before being subjected to a prescribed strain; and
a subsequent air permeability that is less than 18% greater than the initial air permeability after the nonwoven web is subjected to the prescribed strain;
wherein the prescribed strain is at least 10%.

16. The absorbent garment according to claim 15, wherein the basis weight of the nonwoven web ranges from 9 to 16 $g/m^2$.

17. The absorbent garment according to claim 15, wherein the weight of the spunbond fibers in the nonwoven web ranges from 82 to 90% of the basis weight of the nonwoven web.

18. The absorbent garment according to claim 15, wherein at least 80% by weight of the absorbent core is from the superabsorbent polymer material, and the absorbent core includes about 1-40 $g/m^2$ of the hot melt adhesive.

19. The absorbent garment according to claim 15, comprising a topsheet, wherein at least a portion of the topsheet is overlaying the absorbent core, and the overlaying portion is apertured.

20. An absorbent garment comprising:
an absorbent core comprising a superabsorbent polymer material, a hot melt adhesive, and a core cover, wherein the superabsorbent polymer material is more than 80% by weight of the absorbent core, wherein the absorbent core has less than 5% by weight of airfelt material, wherein the core cover surrounds at least a portion of the absorbent core and includes a nonwoven web, and wherein the nonwoven web has:
a layer of meltblown fibers sandwiched between two nonwoven layers of spunbonded fibers, and a weight of the spunbond fibers ranges from 80% to 95% of a basis weight of the nonwoven web; and
an air permeability that is less than 70.8 $m^3/(m^2 \cdot min)$ after the nonwoven web is subjected to a prescribed strain of at least 10%.

\* \* \* \* \*